(12) United States Patent
Dahla et al.

(10) Patent No.: US 8,317,786 B2
(45) Date of Patent: Nov. 27, 2012

(54) SYSTEM, METHOD AND APPARATUS FOR ELECTROSURGICAL INSTRUMENT WITH MOVABLE SUCTION SHEATH

(75) Inventors: Robert H. Dahla, Sunnyvale, CA (US); Irma Gutierrez, San Jose, CA (US)

(73) Assignee: AthroCare Corporation, Austin, TX (US)

( * ) Notice: Subject to any disclaimer, the term of this patent is extended or adjusted under 35 U.S.C. 154(b) by 624 days.

(21) Appl. No.: 12/566,913

(22) Filed: Sep. 25, 2009

(65) Prior Publication Data
US 2011/0077643 A1    Mar. 31, 2011

(51) Int. Cl.
*A61B 18/18*    (2006.01)
*A61B 1/00*    (2006.01)

(52) U.S. Cl. ............... 606/48; 606/41; 604/33; 604/35; 604/119

(58) Field of Classification Search ............. 606/48, 606/50; 604/27, 33, 35, 158, 163, 164.02, 604/181, 183, 30, 40, 118–121, 508; 251/237
See application file for complete search history.

(56) References Cited

U.S. PATENT DOCUMENTS

| | | | |
|---|---|---|---|
| 2,050,904 A | 8/1936 | Trice | 219/233 |
| 2,056,377 A | 10/1939 | Wappler | 125/303 |
| 2,275,167 A | 3/1942 | Bierman | 606/50 |
| 3,633,425 A | 1/1972 | Sanford | 73/356 |
| 3,699,967 A | 10/1972 | Anderson | 606/37 |
| 3,812,858 A | 5/1974 | Oringer | 604/22 |
| 3,815,604 A | 6/1974 | O'Malley et al. | 128/305 |
| 3,828,780 A | 8/1974 | Morrison, Jr. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,945,375 A | 3/1976 | Banko | 600/104 |
| 3,970,088 A | 7/1976 | Morrison | 128/303 |

(Continued)

FOREIGN PATENT DOCUMENTS
DE     2521719     11/1976
(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Linda Dvorak
*Assistant Examiner* — Jaymi Della
(74) *Attorney, Agent, or Firm* — Matthew Scheele; Brian Szymczak

(57) ABSTRACT

An electrosurgical instrument having active and return electrodes with a movable suction sheath for variable fluid and debris removal during surgical procedures is disclosed. The suction apparatus has an outer sheath that is external to a shaft to provide a lumen. The sheath assembly is axially movable relative to the fluid aspiration element between first and second positions for treating the target site and fluid and debris removal, respectively. The first position positions the distal end of the shaft axially distal to a leading edge of the sheath assembly. The second position positions the distal leading edge of the sheath assembly axially adjacent to the end of the shaft. The fluid aspiration element comprises an inner lumen extending through the shaft, and at least one port extending radially through the shaft. The port is in communication with the inner lumen. A vacuum provides suction through the port and inner lumen.

13 Claims, 5 Drawing Sheets

U.S. PATENT DOCUMENTS

| | | | |
|---|---|---|---|
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,203,444 A | 5/1980 | Bonnell et al. | 604/22 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 128/692 |
| 4,248,231 A | 2/1981 | Herczog et al. | 128/303 |
| 4,269,174 A | 5/1981 | Adair | 128/842 |
| 4,326,529 A | 4/1982 | Doss et al. | 128/303 |
| 4,381,007 A | 4/1983 | Doss | 128/303 |
| 4,411,266 A | 10/1983 | Cosman | 606/49 |
| 4,429,694 A | 2/1984 | McGreevy | 128/303.14 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,641,649 A | 2/1987 | Walinsky | 606/33 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 128/303 |
| 4,719,914 A * | 1/1988 | Johnson | 606/28 |
| 4,727,874 A | 3/1988 | Bowers et al. | 128/303 |
| 4,736,743 A | 4/1988 | Daikuzono | 128/303.1 |
| 4,737,678 A | 4/1988 | Hasegawa | 313/36 |
| 4,762,128 A | 8/1988 | Rosenbluth | 128/343 |
| 4,765,331 A | 8/1988 | Petruzzi et al. | 128/303 |
| 4,785,806 A | 11/1988 | Deckelbaum | 128/303.1 |
| 4,785,823 A | 11/1988 | Eggers et al. | 128/692 |
| 4,805,616 A | 2/1989 | Pao | 128/303 |
| 4,813,429 A | 3/1989 | Eshel et al. | 128/736 |
| 4,823,791 A | 4/1989 | D'Amelio et al. | 123/303 |
| 4,827,911 A | 5/1989 | Broadwin et al. | 604/22 |
| 4,832,048 A | 5/1989 | Cohen | 128/786 |
| 4,860,752 A | 8/1989 | Turner et al. | 128/422 |
| 4,903,696 A | 2/1990 | Stasz et al. | 606/37 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,940,064 A | 7/1990 | Desai | 607/122 |
| 4,943,290 A | 7/1990 | Rexroth et al. | 606/45 |
| 4,955,377 A | 9/1990 | Lennox et al. | 128/401 |
| 4,966,597 A | 10/1990 | Cosman | 606/50 |
| 4,967,765 A | 11/1990 | Turner et al. | 128/785 |
| 4,968,314 A | 11/1990 | Michaels | 606/7 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,037,421 A | 8/1991 | Boutacoff et al. | 606/15 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,061,266 A | 10/1991 | Hakky | 606/15 |
| 5,078,717 A | 1/1992 | Parins et al. | 606/48 |
| 5,080,660 A | 1/1992 | Buelna | 606/45 |
| 5,083,565 A | 1/1992 | Parins | 128/642 |
| 5,084,044 A | 1/1992 | Quint | 606/27 |
| 5,084,045 A * | 1/1992 | Helenowski | 606/32 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 128/692 |
| 5,093,877 A | 3/1992 | Aita et al. | 385/34 |
| 5,098,431 A | 3/1992 | Rydell | 606/48 |
| 5,099,840 A | 3/1992 | Goble et al. | 128/422 |
| 5,102,410 A | 4/1992 | Dressel | 606/15 |
| 5,103,804 A | 4/1992 | Abele et al. | 600/116 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,147,354 A | 9/1992 | Boutacoff et al. | 606/15 |
| 5,151,098 A | 9/1992 | Loertscher | 606/16 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,176,528 A | 1/1993 | Fry et al. | 439/181 |
| 5,178,620 A | 1/1993 | Eggers et al. | 606/41 |
| 5,190,517 A | 3/1993 | Zieve et al. | 604/22 |
| 5,191,883 A | 3/1993 | Lennox et al. | 607/102 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,234,428 A | 8/1993 | Kaufman | 606/45 |
| 5,246,438 A | 9/1993 | Langberg | 606/33 |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,269,794 A | 12/1993 | Rexroth | 606/180 |
| 5,273,524 A | 12/1993 | Fox et al. | 604/21 |
| 5,277,201 A | 1/1994 | Stern | 607/98 |
| 5,277,696 A | 1/1994 | Hagen | 606/49 |
| 5,279,299 A | 1/1994 | Imran | 600/393 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,282,799 A | 2/1994 | Rydell | 606/48 |
| 5,290,273 A | 3/1994 | Tan | 606/9 |
| 5,290,282 A | 3/1994 | Casscells | 606/29 |
| 5,293,868 A | 3/1994 | Nardella | 600/373 |
| 5,295,956 A * | 3/1994 | Bales et al. | 604/30 |
| 5,300,069 A | 4/1994 | Hunsberger et al. | 606/37 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,306,238 A | 4/1994 | Fleenor | 606/42 |
| 5,312,395 A | 5/1994 | Tan et al. | 606/9 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,322,507 E | 6/1994 | Costello et al. | 128/4 |
| 5,324,254 A | 6/1994 | Phillips | 604/21 |
| 5,330,470 A | 7/1994 | Hagen | 606/42 |
| 5,330,518 A | 7/1994 | Neilson et al. | 607/101 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,335,668 A | 8/1994 | Nardella | 600/547 |
| 5,336,217 A | 8/1994 | Buys et al. | 606/9 |
| 5,336,220 A | 8/1994 | Ryan et al. | 604/22 |
| 5,336,443 A | 8/1994 | Eggers | 252/511 |
| 5,342,357 A | 8/1994 | Nardella | 606/40 |
| 5,348,554 A | 9/1994 | Imran et al. | 606/41 |
| 5,366,443 A | 11/1994 | Eggers et al. | 604/114 |
| 5,370,642 A | 12/1994 | Keller | 606/9 |
| 5,370,644 A | 12/1994 | Langberg | 606/33 |

| Patent No. | Date | Inventor | Class |
|---|---|---|---|
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita et al. | 606/7 |
| 5,383,876 A | 1/1995 | Nardella | 606/49 |
| 5,383,917 A | 1/1995 | Desai et al. | 607/702 |
| 5,389,096 A | 2/1995 | Aita et al. | 606/15 |
| 5,395,312 A | 3/1995 | Desai | 604/22 |
| 5,395,363 A | 3/1995 | Billings et al. | 606/41 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,405,376 A | 4/1995 | Mulier et al. | 607/127 |
| 5,417,687 A | 5/1995 | Nardella et al. | 606/32 |
| 5,419,767 A | 5/1995 | Eggers et al. | 604/114 |
| 5,445,634 A | 5/1995 | Keller | 606/9 |
| 5,423,803 A | 6/1995 | Tankovich | 606/9 |
| 5,423,810 A | 6/1995 | Goble et al. | 606/40 |
| 5,423,844 A | 6/1995 | Miller | 606/171 |
| 5,423,882 A | 6/1995 | Jackman et al. | 607/122 |
| 5,431,649 A | 7/1995 | Mulier et al. | 606/41 |
| 5,432,882 A | 7/1995 | Jackman et al. | 607/122 |
| 5,433,708 A | 7/1995 | Nichols et al. | 604/113 |
| 5,436,566 A | 7/1995 | Thompson et al. | 324/713 |
| 5,437,662 A | 8/1995 | Nardella | 606/40 |
| 5,437,664 A | 8/1995 | Cohen et al. | 606/42 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,462,545 A | 10/1995 | Wang et al. | 606/41 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,710 A * | 4/1996 | Dorsey, III | 604/158 |
| 5,514,130 A | 5/1996 | Baker | 606/41 |
| 5,520,685 A | 5/1996 | Wojciechowicz | 606/49 |
| 5,536,267 A | 7/1996 | Edwards et al. | 606/41 |
| 5,542,928 A | 8/1996 | Evans et al. | 604/113 |
| 5,545,161 A | 8/1996 | Imran | 606/41 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,579,764 A | 12/1996 | Goldreyer | 600/374 |
| 5,584,872 A | 12/1996 | LaFontaine et al. | 607/116 |
| 5,607,391 A * | 3/1997 | Klinger et al. | 604/33 |
| 5,607,421 A | 3/1997 | Jeevanandam et al. | 606/15 |
| 5,609,151 A | 3/1997 | Mulier et al. | 128/642 |
| 5,626,576 A | 5/1997 | Janssen | 606/41 |
| 5,633,578 A | 5/1997 | Eggers et al. | 323/301 |
| 5,643,255 A | 7/1997 | Organ | 606/41 |
| 5,647,869 A | 7/1997 | Goble et al. | 606/37 |
| 5,653,692 A | 8/1997 | Masterson et al. | 604/113 |
| 5,660,836 A | 8/1997 | Knowlton | 607/116 |
| 5,662,680 A | 9/1997 | Desai | 606/210 |
| 5,676,693 A | 10/1997 | LaFontaine | 607/116 |
| 5,681,282 A | 10/1997 | Eggers et al. | 604/114 |
| 5,681,308 A | 10/1997 | Edwards et al. | 606/41 |
| 5,683,366 A | 11/1997 | Eggers et al. | 604/114 |
| 5,688,267 A | 11/1997 | Panescu et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,713,896 A | 2/1998 | Nardella | 606/50 |
| 5,725,524 A | 3/1998 | Mulier et al. | 606/41 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,766,153 A | 6/1998 | Eggers et al. | 604/114 |
| 5,769,843 A | 6/1998 | Abela et al. | 606/10 |
| 5,769,847 A | 6/1998 | Panescu et al. | 606/42 |
| 5,782,795 A | 7/1998 | Bays | 604/22 |
| 5,785,705 A | 7/1998 | Baker | 606/32 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,843,078 A | 12/1998 | Sharkey | 606/41 |
| 5,855,277 A | 1/1999 | Apps et al. | 606/35 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,871,524 A | 2/1999 | Knowlton | 607/101 |
| 5,873,855 A | 2/1999 | Eggers et al. | 604/114 |
| 5,876,398 A | 3/1999 | Mulier et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,893,848 A | 4/1999 | Negus et al. | 606/41 |
| 5,895,386 A | 4/1999 | Odell et al. | 606/50 |
| 5,897,553 A | 4/1999 | Mulier | 606/41 |
| 5,902,272 A | 5/1999 | Eggers et al. | 604/114 |
| 5,904,681 A | 5/1999 | West, Jr. | 606/41 |
| 5,906,613 A | 5/1999 | Mulier et al. | 606/41 |
| 5,919,219 A | 7/1999 | Knowlton | 607/102 |
| 5,944,715 A | 8/1999 | Goble et al. | 606/41 |
| 5,954,716 A | 9/1999 | Sharkey et al. | 606/32 |
| 5,964,754 A | 10/1999 | Osypka | 606/37 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,004,319 A | 12/1999 | Goble et al. | 606/48 |
| 6,007,533 A | 12/1999 | Casscells et al. | 606/45 |
| 6,007,570 A | 12/1999 | Sharkey et al. | 607/96 |
| 6,013,076 A | 1/2000 | Goble et al. | 606/41 |
| 6,015,406 A | 1/2000 | Goble et al. | 606/41 |
| 6,016,809 A | 1/2000 | Mulier et al. | 128/898 |
| 6,024,733 A | 2/2000 | Eggers et al. | 604/500 |
| 6,027,501 A | 2/2000 | Goble et al. | 606/41 |
| 6,030,383 A | 2/2000 | Benderev | 606/45 |
| 6,032,673 A | 3/2000 | Savage et al. | 128/898 |
| 6,032,674 A | 3/2000 | Eggers et al. | 606/41 |
| 6,039,734 A | 3/2000 | Goble et al. | 606/41 |
| 6,042,580 A | 3/2000 | Simpson | 606/32 |
| 6,045,532 A | 4/2000 | Eggers et al. | 604/114 |
| 6,047,700 A | 4/2000 | Eggers et al. | 128/898 |
| 6,053,172 A | 4/2000 | Hovda et al. | 128/898 |
| 6,056,746 A | 5/2000 | Goble et al. | 606/48 |
| 6,063,079 A | 5/2000 | Hovda et al. | 606/41 |
| 6,063,081 A | 5/2000 | Mulier et al. | 606/45 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,091,995 A | 7/2000 | Ingle et al. | 607/138 |
| 6,093,186 A | 7/2000 | Goble et al. | 606/34 |
| 6,096,037 A | 8/2000 | Mulier et al. | 606/49 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,110,169 A | 8/2000 | Mueller et al. | 606/48 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,152,923 A | 11/2000 | Ryan | 606/51 |
| 6,156,031 A | 12/2000 | Aita et al. | 606/33 |
| 6,159,194 A | 12/2000 | Eggers et al. | 604/500 |

| Patent Number | Kind | Date | Inventor | Class |
|---|---|---|---|---|
| 6,159,208 | A | 12/2000 | Hovda et al. | 606/41 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,203,542 | B1 | 3/2001 | Ellsberry et al. | 606/41 |
| 6,210,402 | B1 | 4/2001 | Olsen et al. | 606/32 |
| 6,210,405 | B1 | 4/2001 | Goble et al. | 606/41 |
| 6,214,001 | B1 | 4/2001 | Casscells et al. | 606/41 |
| 6,217,575 | B1 | 4/2001 | DeVore et al. | 606/41 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,234,178 | B1 | 5/2001 | Goble et al. | 606/32 |
| 6,235,020 | B1 | 5/2001 | Cheng et al. | 606/34 |
| 6,235,023 | B1 | 5/2001 | Lee et al. | 606/41 |
| 6,237,604 | B1 | 5/2001 | Burnside et al. | 128/897 |
| 6,238,391 | B1 | 5/2001 | Olsen et al. | 606/41 |
| 6,238,393 | B1 | 5/2001 | Mulier et al. | 607/127 |
| 6,254,600 | B1 | 7/2001 | Willink et al. | 606/41 |
| 6,261,286 | B1 | 7/2001 | Goble et al. | 606/34 |
| 6,261,311 | B1 | 7/2001 | Sharkey et al. | 607/96 |
| 6,264,650 | B1 | 7/2001 | Hovda | 606/32 |
| 6,264,652 | B1 | 7/2001 | Eggers et al. | 606/41 |
| 6,267,757 | B1 | 7/2001 | Aita et al. | 606/33 |
| 6,270,460 | B1 | 8/2001 | McCartan et al. | 600/459 |
| 6,277,112 | B1 | 8/2001 | Underwood et al. | 606/32 |
| 6,280,441 | B1 | 8/2001 | Ryan | 606/45 |
| 6,283,961 | B1 | 9/2001 | Underwood et al. | 606/41 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,302,903 | B1 | 10/2001 | Mulier et al. | 607/105 |
| 6,306,134 | B1 | 10/2001 | Goble et al. | 606/42 |
| 6,308,089 | B1 | 10/2001 | von der Ruhr et al. | 600/338 |
| 6,309,387 | B1 | 10/2001 | Eggers et al. | 606/41 |
| 6,312,408 | B1 | 11/2001 | Eggers et al. | 604/114 |
| 6,312,429 | B1 | 11/2001 | Butbank et al. | 606/47 |
| 6,315,774 | B1 | 11/2001 | Daniel et al. | 606/15 |
| 6,322,494 | B1 | 11/2001 | Bullivant et al. | 600/104 |
| 6,322,549 | B1 | 11/2001 | Eggers et al. | 604/500 |
| 6,325,799 | B1 | 12/2001 | Goble | 606/41 |
| 6,327,505 | B1 | 12/2001 | Medhkour et al. | 607/99 |
| 6,328,736 | B1 | 12/2001 | Mulier et al. | 606/45 |
| 6,336,926 | B1 | 1/2002 | Goble | 606/34 |
| 6,346,107 | B1 | 2/2002 | Cucin | 606/49 |
| 6,355,006 | B1 | 3/2002 | Ryaby et al. | 601/2 |
| 6,355,032 | B1 | 3/2002 | Hovda et al. | 606/32 |
| 6,358,248 | B1 | 3/2002 | Mulier et al. | 606/41 |
| 6,363,937 | B1 | 4/2002 | Hovda et al. | 128/898 |
| 6,364,877 | B1 | 4/2002 | Goble et al. | 606/34 |
| 6,379,350 | B1 | 4/2002 | Sharkley et al. | 606/41 |
| 6,379,351 | B1 | 4/2002 | Thapliyal et al. | 606/41 |
| 6,391,025 | B1 | 5/2002 | Weinstein et al. | 606/41 |
| 6,391,028 | B1 | 5/2002 | Fanton et al. | 606/45 |
| 6,398,781 | B1 | 6/2002 | Goble et al. | 606/41 |
| 6,409,724 | B1 | 6/2002 | Penny et al. | 606/41 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |
| 6,432,103 | B1 | 8/2002 | Ellsberry et al. | 606/41 |
| 6,432,105 | B1 | 8/2002 | Ellman et al. | 606/48 |
| 6,468,274 | B1 | 10/2002 | Alleyne et al. | 606/32 |
| 6,468,275 | B1 | 10/2002 | Wampler et al. | 606/48 |
| 6,482,201 | B1 | 11/2002 | Olsen et al. | 606/41 |
| 6,482,202 | B1 | 11/2002 | Goble et al. | 606/41 |
| 6,491,690 | B1 | 12/2002 | Goble et al. | 606/41 |
| 6,497,705 | B2 * | 12/2002 | Comben | 606/41 |
| 6,497,706 | B1 * | 12/2002 | Burbank et al. | 606/45 |
| 6,510,854 | B2 | 1/2003 | Goble | 128/898 |
| 6,514,250 | B1 | 2/2003 | Jahns et al. | 606/41 |
| 6,517,498 | B1 | 2/2003 | Burbank et al. | 600/564 |
| 6,517,535 | B2 | 2/2003 | Edwards | 606/41 |
| 6,530,922 | B2 | 3/2003 | Cosman | 606/34 |
| 6,540,741 | B1 | 4/2003 | Underwood et al. | 606/32 |
| 6,557,559 | B1 | 5/2003 | Eggers et al. | 128/898 |
| 6,575,968 | B1 | 6/2003 | Eggers et al. | 606/41 |
| 6,575,969 | B1 | 6/2003 | Rittman, III et al. | 606/41 |
| 6,578,579 | B2 | 6/2003 | Burnside | 128/897 |
| 6,582,423 | B1 | 6/2003 | Thapliyal et al. | 606/32 |
| 6,589,237 | B2 | 7/2003 | Woloszko et al. | 606/41 |
| 6,595,990 | B1 | 7/2003 | Weinstein et al. | 606/41 |
| 6,597,950 | B2 | 7/2003 | Linder et al. | 607/8 |
| 6,602,248 | B1 | 8/2003 | Sharps et al. | 606/32 |
| 6,605,085 | B1 | 8/2003 | Edwards | 606/41 |
| 6,610,059 | B1 | 8/2003 | West, Jr. | 606/41 |
| 6,620,156 | B1 | 9/2003 | Garito et al. | 606/50 |
| 6,632,193 | B1 | 10/2003 | Davison et al. | 604/22 |
| 6,632,220 | B1 | 10/2003 | Eggers et al. | 606/41 |
| 6,632,230 | B2 | 10/2003 | Barry | 606/159 |
| 6,645,203 | B2 | 11/2003 | Sharkey et al. | 606/41 |
| 6,663,628 | B2 | 12/2003 | Peters | 606/45 |
| 6,695,839 | B2 | 2/2004 | Sharkey et al. | 606/49 |
| 6,699,206 | B2 | 3/2004 | Burbank et al. | 606/567 |
| 6,699,244 | B2 | 3/2004 | Carranza et al. | 606/41 |
| 6,702,810 | B2 | 3/2004 | McClurken et al. | 606/34 |
| 6,746,447 | B2 | 6/2004 | Davison et al. | 606/41 |
| 6,749,604 | B1 | 6/2004 | Eggers et al. | 606/41 |
| 6,749,608 | B2 | 6/2004 | Garito et al. | 606/45 |
| 6,763,836 | B2 | 7/2004 | Tasto et al. | 128/898 |
| 6,770,071 | B2 | 8/2004 | Woloszko et al. | 606/41 |
| 6,780,178 | B2 | 8/2004 | Palanker et al. | 600/41 |
| 6,780,180 | B1 | 8/2004 | Goble et al. | 606/41 |
| 6,796,982 | B2 | 9/2004 | Carmel et al. | 606/41 |
| 6,802,842 | B2 | 10/2004 | Ellman et al. | 606/45 |
| 6,805,130 | B2 | 10/2004 | Tasto et al. | 606/32 |
| 6,827,725 | B2 | 12/2004 | Batchelor et al. | 606/170 |
| 6,832,996 | B2 | 12/2004 | Woloszko et al. | 606/41 |
| 6,837,887 | B2 | 1/2005 | Woloszko et al. | 606/41 |
| 6,837,888 | B2 | 1/2005 | Ciarrocca et al. | 606/41 |
| 6,855,143 | B2 | 2/2005 | Davison et al. | 606/41 |
| 6,896,674 | B1 | 5/2005 | Woloszko et al. | 606/41 |
| 6,904,303 | B2 | 6/2005 | Phan et al. | 600/374 |
| 6,920,883 | B2 | 7/2005 | Bessette et al. | 128/898 |
| 6,929,640 | B1 | 8/2005 | Underwood et al. | 606/32 |
| 6,949,096 | B2 | 9/2005 | Davison et al. | 606/41 |
| 6,960,204 | B2 | 11/2005 | Eggers et al. | 606/32 |
| 6,974,453 | B2 | 12/2005 | Woloszko et al. | 606/41 |
| 6,979,332 | B2 | 12/2005 | Adams | 606/45 |
| 6,984,231 | B2 | 1/2006 | Goble et al. | 606/37 |
| 6,991,631 | B2 | 1/2006 | Woloszko et al. | 606/41 |
| 7,004,941 | B2 | 2/2006 | Tvinnereim et al. | 606/41 |
| 7,041,102 | B2 | 5/2006 | Truckai et al. | 606/51 |
| 7,070,596 | B1 | 7/2006 | Woloszko et al. | 606/41 |
| 7,090,672 | B2 | 8/2006 | Underwood et al. | 606/41 |
| 7,094,215 | B2 | 8/2006 | Davison et al. | 604/22 |
| 7,104,986 | B2 | 9/2006 | Hovda et al. | 606/32 |
| 7,131,969 | B1 | 11/2006 | Hovda et al. | 606/45 |
| 7,150,747 | B1 | 12/2006 | McDonald et al. | 606/45 |
| 7,169,143 | B2 | 1/2007 | Eggers et al. | 606/32 |
| 7,179,255 | B2 | 2/2007 | Lettice et al. | 606/32 |
| 7,184,811 | B2 | 2/2007 | Phan et al. | 600/374 |
| 7,186,234 | B2 | 3/2007 | Dahla et al. | 604/22 |
| 7,192,428 | B2 | 3/2007 | Eggers et al. | 606/41 |
| 7,201,750 | B1 | 4/2007 | Eggers et al. | 606/41 |
| 7,217,268 | B2 | 5/2007 | Eggers et al. | 606/32 |
| 7,241,293 | B2 | 7/2007 | Davison | 600/410 |
| 7,258,690 | B2 | 8/2007 | Sutton et al. | 606/45 |
| 7,261,712 | B2 | 8/2007 | Burbank et al. | 606/49 |
| 7,270,658 | B2 | 9/2007 | Woloszko et al. | 606/32 |
| 7,270,659 | B2 | 9/2007 | Hovda et al. | 606/32 |
| 7,270,661 | B2 | 9/2007 | Dahla et al. | 606/41 |
| 7,276,063 | B2 | 10/2007 | Davison et al. | 606/45 |
| 7,297,143 | B2 | 11/2007 | Woloszko et al. | 606/41 |
| 7,297,145 | B2 | 11/2007 | Ormbsy et al. | 606/41 |
| 7,318,823 | B2 | 1/2008 | Sharps et al. | 606/32 |
| 7,331,956 | B2 | 2/2008 | Hovda et al. | 606/32 |
| RE40,156 | E | 3/2008 | Sharps et al. | 606/32 |
| 7,357,798 | B2 | 4/2008 | Sharps et al. | 606/32 |
| 7,387,625 | B2 | 6/2008 | Hovda et al. | 606/32 |
| 7,419,488 | B2 | 9/2008 | Ciarrocca et al. | 606/41 |
| 7,429,260 | B2 | 9/2008 | Underwood et al. | 606/32 |
| 7,429,262 | B2 | 9/2008 | Woloszko et al. | 606/46 |
| 7,435,247 | B2 | 10/2008 | Woloszko et al. | 604/45 |
| 7,442,191 | B2 | 10/2008 | Hovda et al. | 606/41 |
| 7,445,618 | B2 | 11/2008 | Eggers et al. | 604/48 |

| | | | | | | |
|---|---|---|---|---|---|---|
| 7,449,021 | B2 | 11/2008 | Underwood et al. ............ 606/32 | EP | 0 754 437 | 1/1997 |
| 7,462,178 | B2 | 12/2008 | Woloszko et al. ............. 607/105 | EP | 923907 | 6/1999 |
| 7,468,059 | B2 | 12/2008 | Eggers et al. ................... 606/32 | EP | 0 694 290 | 11/2000 |
| 7,488,295 | B2 | 2/2009 | Burbank et al. ............... 606/167 | EP | 1149564 | 10/2001 |
| 7,491,200 | B2 | 2/2009 | Underwood et al. ............ 606/32 | EP | 1041933 | 3/2004 |
| 7,507,236 | B2 | 3/2009 | Eggers et al. ................... 606/41 | FR | 2313949 | 1/1977 |
| 7,572,251 | B1 | 8/2009 | Davison et al. ................ 604/500 | GB | 2037167 | 7/1980 |
| 7,776,034 | B2 | 8/2010 | Kampa ............................ 606/41 | GB | 2 308 979 | 7/1997 |
| 7,819,863 | B2 | 10/2010 | Eggers et al. ................... 606/32 | GB | 2 308 980 | 7/1997 |
| 8,038,670 | B2 | 10/2011 | McClurken ..................... 606/41 | GB | 2 308 981 | 7/1997 |
| 2002/0029036 | A1 | 3/2002 | Goble et al. ..................... 606/38 | GB | 2 327 350 | 1/1999 |
| 2002/0049438 | A1 | 4/2002 | Sharkey et al. ................. 606/41 | GB | 2 327 351 | 1/1999 |
| 2002/0072739 | A1 | 6/2002 | Lee et al. ......................... 606/47 | GB | 2 327 352 | 1/1999 |
| 2003/0013986 | A1 | 1/2003 | Saadat ............................ 600/549 | GB | 2331247 | 5/1999 |
| 2003/0088245 | A1 | 5/2003 | Woloszko et al. ............... 606/41 | GB | 2379878 | 3/2003 |
| 2003/0130655 | A1 | 7/2003 | Woloszko et al. ............... 606/45 | GB | 2408936 | 6/2005 |
| 2003/0130711 | A1 | 7/2003 | Pearson et al. ................. 607/101 | JP | 57-57802 | 4/1982 |
| 2003/0158545 | A1 | 8/2003 | Hovda et al. .................... 606/32 | JP | 57-117843 | 7/1982 |
| 2003/0171743 | A1 | 9/2003 | Tasto et al. ...................... 606/32 | JP | 57-183850 | 11/1982 |
| 2003/0208196 | A1 | 11/2003 | Stone ............................... 606/41 | JP | 63-40099 | 8/1988 |
| 2003/0212396 | A1 | 11/2003 | Eggers et al. ................... 606/41 | JP | 9-501328 | 2/1997 |
| 2004/0116922 | A1 | 6/2004 | Hovda et al. .................... 606/41 | WO | 90/03152 | 4/1990 |
| 2004/0127893 | A1 | 7/2004 | Hovda ............................. 606/41 | WO | 90/07303 | 7/1990 |
| 2004/0230190 | A1 | 11/2004 | Dahla et al. ..................... 604/41 | WO | 91/13650 | 9/1991 |
| 2005/0004634 | A1 | 1/2005 | Hovda et al. .................... 606/41 | WO | 92/21278 | 12/1992 |
| 2005/0119650 | A1 | 6/2005 | Sanders et al. ................ 424/426 | WO | 93/13816 | 7/1993 |
| 2005/0251134 | A1 | 11/2005 | Woloszko et al. ............... 606/32 | WO | 93/20747 | 10/1993 |
| 2005/0261754 | A1 | 11/2005 | Woloszko et al. ............... 606/32 | WO | 94/03134 | 2/1994 |
| 2005/0288665 | A1 | 12/2005 | Woloszko et al. ............... 606/41 | WO | 94/04220 | 3/1994 |
| 2006/0036237 | A1 | 2/2006 | Davison et al. .................. 606/41 | WO | 94/08654 | 4/1994 |
| 2006/0095031 | A1 | 5/2006 | Ormsby ........................... 606/34 | WO | 94/10924 | 5/1994 |
| 2006/0106379 | A1* | 5/2006 | O'Brien et al. .................. 606/45 | WO | 94/14383 | 7/1994 |
| 2006/0178670 | A1 | 8/2006 | Woloszko et al. ............... 606/48 | WO | 94/26228 | 11/1994 |
| 2006/0189971 | A1 | 8/2006 | Eggers et al. ................... 606/41 | WO | 95/05780 | 3/1995 |
| 2006/0253117 | A1 | 11/2006 | Hovda et al. .................. 128/898 | WO | 95/05781 | 3/1995 |
| 2006/0259025 | A1 | 11/2006 | Dahla ............................ 607/108 | WO | 95/05867 | 3/1995 |
| 2007/0005051 | A1* | 1/2007 | Kampa ............................ 606/41 | WO | 95/10326 | 4/1995 |
| 2007/0010808 | A1 | 1/2007 | Dahla .............................. 606/41 | WO | 95/30373 | 11/1995 |
| 2007/0106288 | A1 | 5/2007 | Woloszko et al. ............... 606/41 | WO | 95/34259 | 12/1995 |
| 2007/0149966 | A1 | 6/2007 | Dahla et al. ..................... 606/41 | WO | 96/00042 | 1/1996 |
| 2007/0161981 | A1 | 7/2007 | Sanders et al. .................. 606/41 | WO | 96/07360 | 3/1996 |
| 2007/0208334 | A1 | 9/2007 | Woloszko et al. ............... 606/41 | WO | 96/34568 | 11/1996 |
| 2007/0208335 | A1 | 9/2007 | Woloszko et al. ............... 606/41 | WO | 96/35469 | 11/1996 |
| 2007/0213700 | A1 | 9/2007 | Davison et al. .................. 606/32 | WO | 96/39914 | 12/1996 |
| 2007/0282323 | A1 | 12/2007 | Woloszko et al. ............... 606/41 | WO | 96/39962 | 12/1996 |
| 2008/0021447 | A1 | 1/2008 | Davison et al. .................. 606/41 | WO | 96/39964 | 12/1996 |
| 2008/0167645 | A1 | 7/2008 | Woloszko ........................ 606/40 | WO | 96/39965 | 12/1996 |
| 2008/0167646 | A1 | 7/2008 | Godara et al. ................... 606/41 | WO | 96/39967 | 12/1996 |
| 2008/0234673 | A1 | 9/2008 | Marion et al. ................... 606/45 | WO | 97/00646 | 1/1997 |
| 2008/0300590 | A1 | 12/2008 | Horne et al. ..................... 606/35 | WO | 97/00647 | 1/1997 |
| 2009/0069807 | A1 | 3/2009 | Eggers et al. ................... 606/48 | WO | 97/15238 | 5/1997 |
| 2009/0138011 | A1 | 5/2009 | Epstein ............................ 606/42 | WO | 97/18765 | 5/1997 |
| 2009/0209958 | A1 | 8/2009 | Davison et al. .................. 606/41 | WO | 97/24073 | 7/1997 |
| 2010/0042095 | A1 | 2/2010 | Bigley et al. .................... 606/41 | WO | 97/24074 | 7/1997 |
| 2010/0152724 | A1 | 6/2010 | Marion et al. ................... 606/41 | WO | 97/24992 | 7/1997 |
| 2010/0204690 | A1 | 8/2010 | Bigley et al. .................... 606/41 | WO | 97/24993 | 7/1997 |
| 2011/0077646 | A1 | 3/2011 | Dahla et al. ..................... 606/50 | WO | 97/24994 | 7/1997 |
| 2011/0270242 | A1 | 11/2011 | Marion ............................ 606/35 | WO | 97/25101 | 7/1997 |
| 2012/0179157 | A1 | 7/2012 | Frazier et al. ................... 606/41 | WO | 97/32551 | 9/1997 |
| | | | | WO | 97/33523 | 9/1997 |
| | | FOREIGN PATENT DOCUMENTS | | WO | 97/34540 | 9/1997 |
| DE | | 3930451 A1 | 3/1991 | WO | 97/41786 | 11/1997 |
| DE | | 4425015 | 1/1996 | WO | 97/44071 | 11/1997 |
| DE | | 296 09 350 | 8/1996 | WO | 97/48345 | 12/1997 |
| DE | | 195 37 084 | 4/1997 | WO | 97/48346 | 12/1997 |
| DE | | 296 19 029 | 4/1997 | WO | 98/07468 | 2/1998 |
| DE | | 19850671 | 5/1999 | WO | 98/14131 | 4/1998 |
| DE | | 10254668 | 6/2004 | WO | 98/17185 | 4/1998 |
| DE | | 69822877 | 1/2005 | WO | 98/17186 | 4/1998 |
| DE | | 202008000276 | 6/2008 | WO | 98/27877 | 7/1998 |
| DE | | 102009057921 A1 | 6/2010 | WO | 98/27879 | 7/1998 |
| EP | | 0 502 268 | 9/1992 | WO | 98/27880 | 7/1998 |
| EP | | 0 515 867 | 12/1992 | WO | 98/30144 | 7/1998 |
| EP | | 543123 | 5/1993 | WO | 98/34550 | 8/1998 |
| EP | | 0 597 463 | 5/1994 | WO | 98/34558 | 8/1998 |
| EP | | 774926 | 3/1995 | WO | 98/38925 | 9/1998 |
| EP | | 0 650 701 | 5/1995 | WO | 98/39038 | 9/1998 |
| EP | | 0703461 A2 | 3/1996 | WO | 99/00060 | 1/1999 |
| EP | | 0740926 A2 | 11/1996 | WO | 99/20185 | 4/1999 |

| WO | 99/42037 | 8/1999 |
| WO | 99/44506 | 9/1999 |
| WO | 99/51155 | 10/1999 |
| WO | 99/51158 | 10/1999 |
| WO | 00/09053 | 2/2000 |
| WO | 01/26570 | 4/2001 |
| WO | 01/87154 | 5/2001 |
| WO | 01/95819 | 12/2001 |
| WO | 02/36028 | 5/2002 |
| WO | 02/78557 | 10/2002 |
| WO | 03/024339 | 3/2003 |
| WO | 2005/125287 | 12/2005 |
| WO | 2008/073727 | 6/2008 |
| WO | 2009/094392 | 7/2009 |
| WO | 2011/071482 | 6/2011 |

OTHER PUBLICATIONS

Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" Crc Press, 3 pgs 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164 pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
BiLAP IFU 910026-001 Rev A for BiLAP Model 3525, J-Hook, 4 pgs, May 20, 1991.
BiLAP Generator Settings, Jun. 1991.
Tucker et al. "The interaction between electrosurgical generators, endroscopic electrodes, and tissue," Gastrointestinal Endoscopy, vol. 38, No. 2, pp. 118-122, 1992.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Hardy et al., "Regional Myocardial Blood Flow and Cardiac mechanics in dog Hearts with CO2 laser-induced Intramyocardial Revascularization", Basic Research in cardiology 85:179-196, 1990.
Mirhoseini et al., "New Concepts in Revascularization of the Myocardium", Ann Thorac Surg 45:415-420 (1988).
Mirhoseini et al., "Revascularization of the heart by Laser", J. of Microsurgery 2:253-260 (1981).
Mirhoseini et al., "Transmyocardial Laser Revascularization: A Review", J. of Clinical Laser medicine & Surgery 11 (1) :15-19 (1993).
Mirhoseini et al., "Transventricular Revascularization by Laser", Lasers in Surgery and Medicine 2:187-198 (1982).
Rand et al., "Effect of Elecctrocautery on Fresh Human Articular Cartilage", J. Arthro. Surg., vol. 1, pp. 242-246, 1985.
Walter et al., "Treatment of Acute Mycardial Infarction by Transmural Blood Supply from the Ventricular Cavity", Erop. Surgery Res. 3:130-138 (1971).
Whittaker et al., "Transmural Channels Can Protect Ischemic Tissue", Circulation 93(1):143-152, Jan. 1, 1996.
EP Search Report for EP01124768 2 pgs, Nov. 30, 2001.
EP Search Report for EP01935650 10 pgs, Mailed Jul. 26, 2006.
EP Search Report for EP01935650 8 pgs, Mailed May 3, 2005.
EP Search Report for EP02768969 3 pgs, Mailed Feb. 12, 2007.
EP Search Report for EP03762238 3 pgs, Mailed Jun. 2, 2006.
EP Search Report for EP94916716 2 pgs, Oct. 29, 1996.
EP Search Report for EP96941386 2 pgs, Nov. 27, 1998.
EP Search Report for EP98952032 2 pgs, Nov. 24, 2000.
EP Search Report for EP 03736488 3 pgs, Mailed Jun. 25, 2009.
PCT International Search Report for PCT/US00/07718 1 pg, Mailed Sep. 5, 2000.
PCT International Search Report for PCT/US01/16006, 1 pg, Mailed Aug. 14, 2001.
PCT International Search Report for PCT/US02/31640 1 pg, Mailed May 23, 2003.
PCT International Search Report for PCT/US03/04689 1 pg, Mailed Sep. 26, 2003.
PCT International Search Report for PCT/US03/12790 1 pg, Mailed Aug. 12, 2003.
PCT International Search Report for PCT/US03/20574 1 pg, Mailed May 25, 2005.
PCT International Search Report for PCT/US04/22803 1 pg, Mailed Apr. 29, 2005.
PCT International Search Report for PCT/US05/07038 1 pg, Mailed Sep. 2, 2005.
PCT International Search Report for PCT/US94/05168, 1 pg, Mailed Oct. 18, 1994.
PCT International Search Report for PCT/US98/20768 1 pg, Mailed Jan. 20, 1999.
PCT International Search Report for PCT/US98/22327 1 pg, Mailed Feb. 9, 1999.
PCT IPER for PCT/US01/16006 3pgs, Apr. 16, 2002.
PCT IPER for PCT/US98/22327 4pgs, Aug. 27, 2000.
PCT Written Opinion for PCT/US04/22803 3pgs, Mailed Apr. 29, 2005.
PCT Written Opinion for PCT/US05/07038 3pgs, Mailed Sep. 2, 2005.
UK Search Report for GB0805061.9 1 pg, Jul. 15, 2008.
EP Search Report for EP 07118068 3pgs, Mailed Dec. 27, 2010.
EP Search Report for EP 04778347 4pgs, Feb. 22, 2011.
PCT International Search Report for PCT/US96/18505, 3 pgs, Mailed Jan. 17, 1997.
PCT Notif of the Int'l Search Report and Written Opinion for PCT/US09/67001 6 pgs, Mailed Jan. 29, 2010.
UK Search Report for GB0921635.9 3pgs, Apr. 12, 2010.
UK Search Report for GB1106425.0 6 pages, Aug. 16, 2011.
UK combined Search and Examination Report for GB1121048.1 3pgs, Apr. 18, 2012.

* cited by examiner

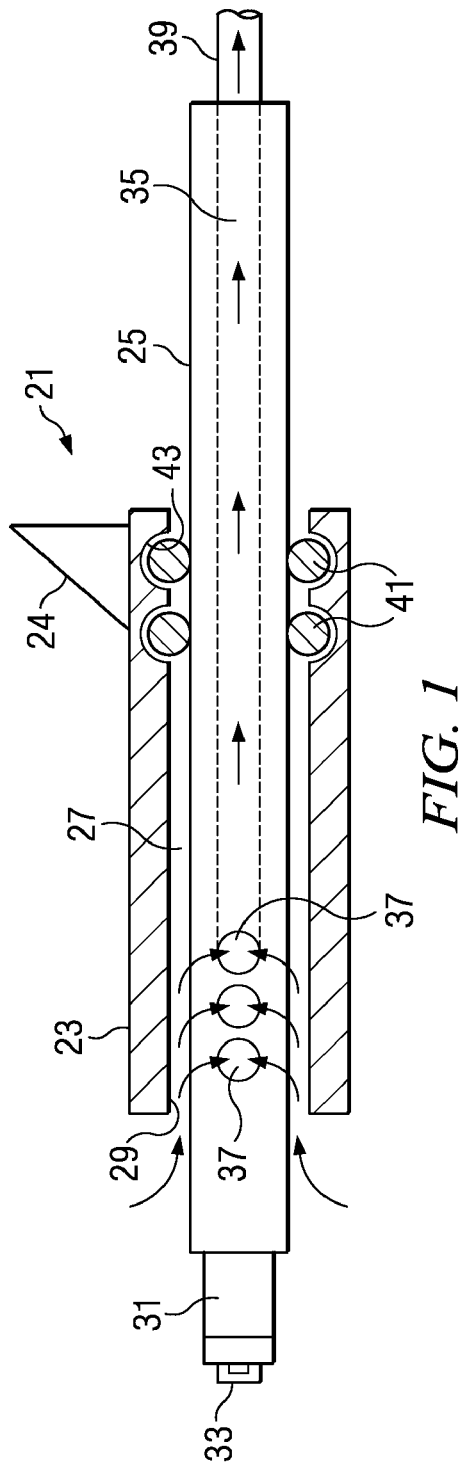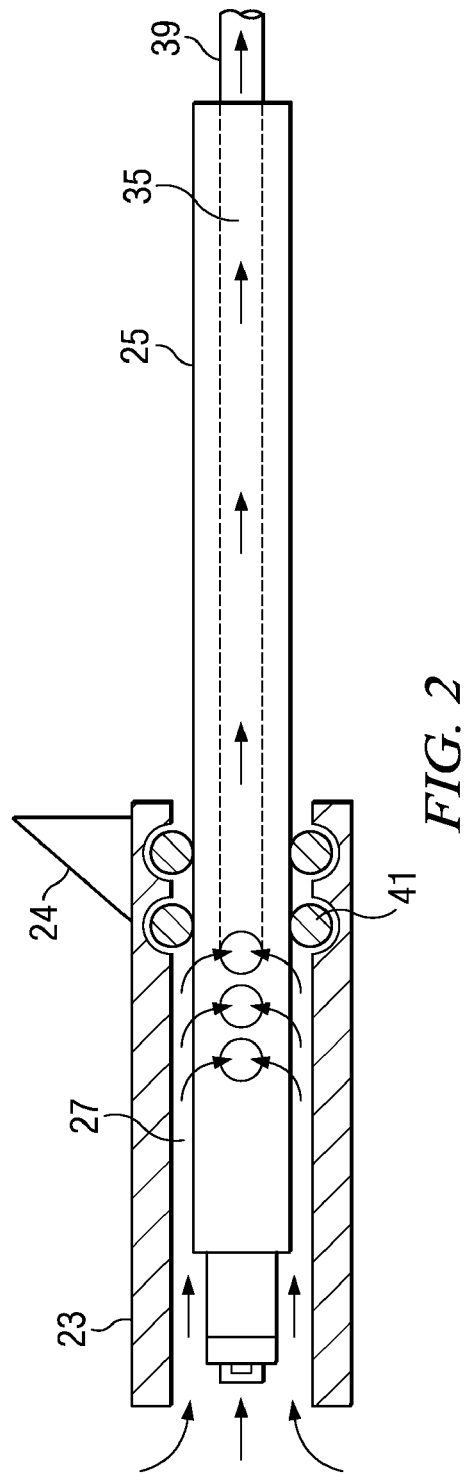

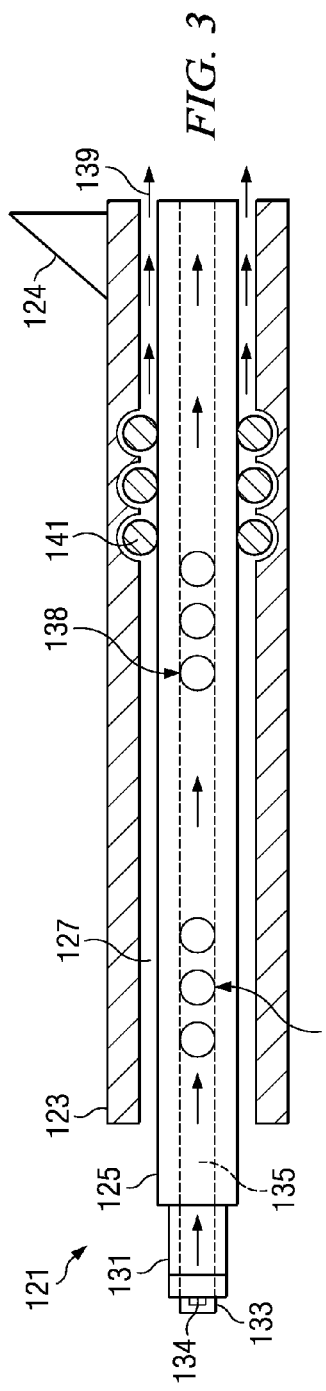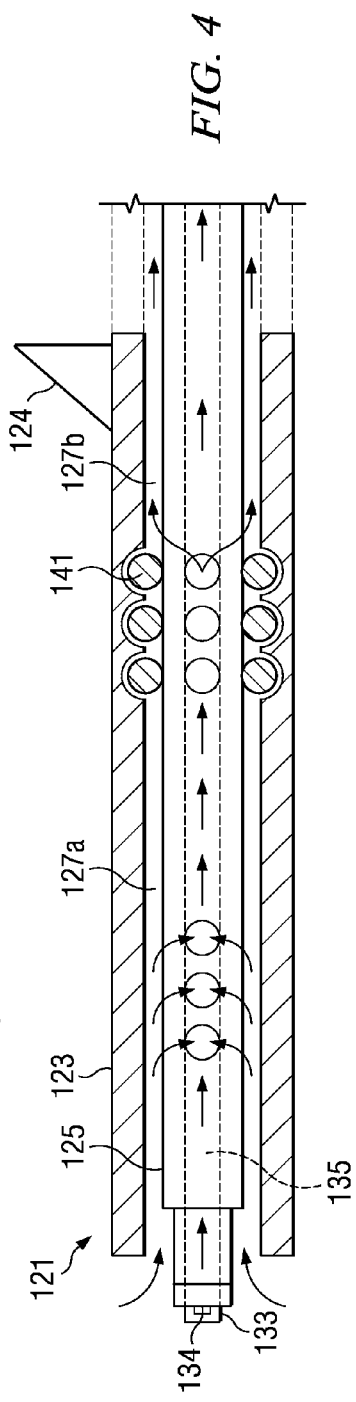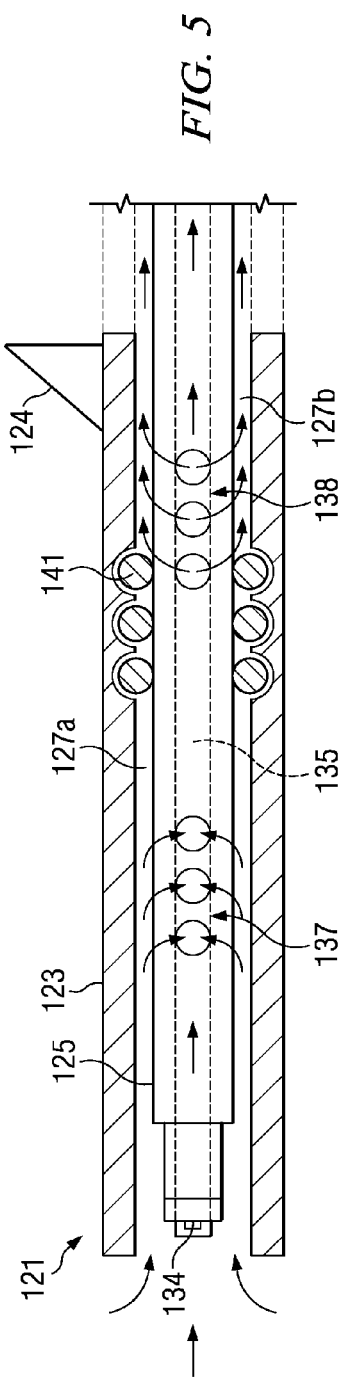

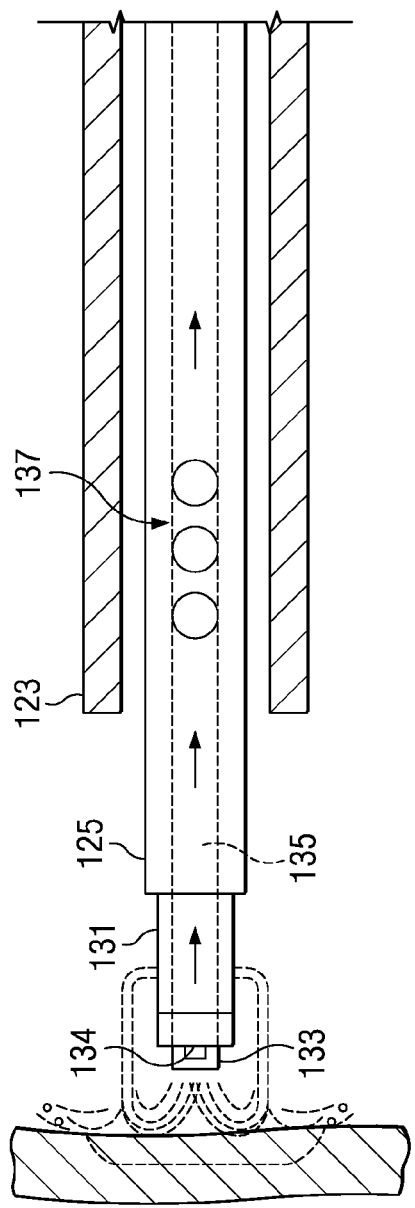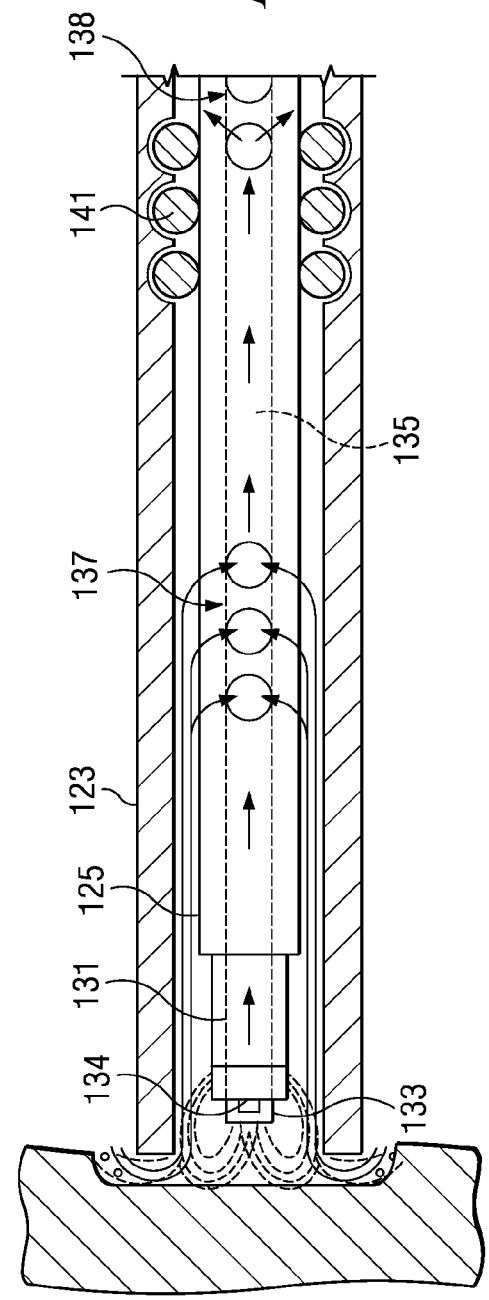

SYSTEM, METHOD AND APPARATUS FOR ELECTROSURGICAL INSTRUMENT WITH MOVABLE SUCTION SHEATH

TECHNICAL FIELD

The present invention relates in general to electrosurgical instruments and, in particular, to an electrosurgical instrument with a fluid aspiration device for controllably removing fluid from a treatment site. More particularly, the present invention relates to a system, method and apparatus for an electrosurgical instrument having active and return electrodes with a movable suction sheath for variable fluid and debris removal during surgical procedures.

DESCRIPTION OF THE RELATED ART

In some electrosurgical procedures an instrument (see, e.g., U.S. Pat. Nos. 5,683,366 and 6,235,020, which are incorporated herein by reference) has an active electrode and a return electrode that are used to treat body tissue. Treatment with this instrument may include, for example, coagulation, cutting, ablating, abrading or puncturing the tissue. In various designs, a current path is created between the active and return electrodes, thereby generating a limited plasma field between the electrodes and applying the plasma to the tissue, preferably without passing the current through the tissue. The current path may be created by providing an electrically conductive fluid at the target, or in some instances immersing the target site within electrically conductive fluid. It is preferred that the electrically conductive fluid has sufficient conductivity such that the fluid is ionized when subject to sufficient radio frequency (RF) electrical energy to thereby form the limited plasma. The conductive fluid path is an electrolyte, such as saline, lactated ringers solution, or conductive gels. One of the electrodes, referred to as the active electrode, is designed to generate a higher current density relative to other electrode, which is referred to as the return electrode. The source of the current is a high frequency voltage applied across the electrodes.

Conventional electrosurgical cutting or resecting devices tend to leave the operating field cluttered with tissue fragments that have been removed or resected from the target tissue. To maintain proper visualization of the surgical site, these fragments and ablative byproducts are periodically or continuously aspirated from the treatment site. Some electrosurgical instruments, such as U.S. Pat. No. 6,589,237, and U.S. Pat. App. Pub. 2006/0259025, which are incorporated herein by reference, employ a vacuum system having a suction inlet on a distal end portion to aspirate resected tissue fragments and ablation byproducts such as fluid and gas bubbles. The vacuum system is disposed at least partly within a lumen defined by an elongate member. Preferably, the instrument maintains a conductive fluid bridge and resultant plasma field between the electrodes during use regardless of the orientation of the electrodes relative to the target tissue and regardless of the operation of the vacuum aspiration element.

For some applications, electrosurgical instruments with these types of aspiration systems provide insufficient fluid and debris removal from the treatment site. Aspiration may be too slow because the aspiration rate is limited by the shaft size, or may be prone to clogging. Although separate or additional aspiration systems may be employed for such applications, they add significant cost and complication to such procedures, while requiring multiple suctions lines and crowding of the surgical area. Further, certain procedures may require aspiration of relatively large volumes of fluid from the target site, resulting in difficulties in generating and maintaining a plasma from the ionized electrically conductive fluid in the vicinity of the active electrode. Thus, an improved solution that overcomes the limitations of the prior art would be desirable.

BRIEF SUMMARY OF THE INVENTION

Embodiments of a system, method, and apparatus for an electrosurgical instrument having active and return electrodes with a movable suction sheath for variable fluid and debris removal during surgical procedures are disclosed. The electrosurgical suction apparatus has an outer sheath that is external to a shaft to provide an annular fluid and debris removal channel or lumen. The sheath assembly is axially slidable and movable relative to the fluid aspiration element between first and second positions for treating the target site and controllable fluid and debris removal, respectively. The first position comprises positioning the distal leading edge of the sheath assembly axially proximal to the distal end of the shaft. The second position may comprise positioning the distal leading edge of the sheath assembly axially adjacent to the distal end of the shaft, or axially distal to the distal end of the shaft.

The fluid aspiration element comprises an inner lumen extending through the shaft, and at least one port extending radially through the shaft. The at least one port is in fluid communication with the inner lumen. A vacuum source is connected to the inner lumen for providing suction through the port and inner lumen. In one embodiment, the sheath assembly comprises a tube that is slidably movable relative to and concentric with the shaft. The tube defines an annular space or outer lumen between the tube and the shaft and has a radial seal. The radial seal is disposed between an outer surface of the shaft and an inner surface of the tube and sealingly engages the shaft and the tube.

In another embodiment, the sheath assembly has a range of motion between the first and second positions that provides a variable level of fluid and debris removal. Preferably, the sheath assembly is movable to provide a minimal level of fluid and debris removal in the first position, to a maximum level of fluid and debris removal in the second position. The fluid aspiration element comprises an inner lumen extending through a portion of the shaft, and first and second plurality of ports extending radially through the shaft in fluid communication with the inner lumen. The first and second plurality of ports are preferably axially spaced apart. A vacuum source is connected to the inner lumen and to the outer lumen proximal to the radial seal. Aspiration is preferably provided only through an opening to the inner lumen at the distal end of the shaft when the sheath assembly is in the first position despite the outer lumen proximal the radial seals being under vacuum pressure, as the radial seal creates a bypass preventing aspiration through the outer lumen and first and second plurality of ports. When the sheath assembly is in an intermediate or second position, the vacuum source may provide a sequential suction path through the inner lumen as well as through the outer lumen that is distal to the radial seal, the first plurality of ports, and the second plurality of ports via the outer lumen proximal to the radial seal.

The invention may further comprise a method for treating tissue including the steps of positioning an active electrode adjacent to tissue; applying a first high frequency voltage between the active electrode and a return electrode; positioning a sheath assembly in a first position, the first position creating an aspiration region around the active electrode; aspirating fluid from the region adjacent to the active electrode; retracting the sheath assembly to a second position; advancing the active electrode into the tissue; applying a second high frequency voltage between the return electrode and a coagulation electrode; and returning the sheath assembly to the first position to aspirate fluid from a region axially spaced away from the active electrode.

The foregoing and other objects and advantages of the present invention will be apparent to those skilled in the art, in view of the following detailed description of the present invention, taken in conjunction with the appended claims and the accompanying drawings.

BRIEF DESCRIPTION OF THE DRAWINGS

So that the manner in which the features and advantages of the present disclosure are attained and can be understood in more detail, a more particular description of the apparatus and methods briefly summarized above may be had by reference to the embodiments thereof that are illustrated in the appended drawings. However, the drawings illustrate only some embodiments of this disclosure and therefore are not to be considered limiting of its scope as the invention may admit to other equally effective embodiments.

FIG. 1 is a sectional side view of one embodiment of an electrosurgical instrument shown in a first position and is constructed in accordance with the invention;

FIG. 2 is a sectional side view of the electrosurgical instrument of FIG. 1, shown in a second position, and is constructed in accordance with the invention;

FIGS. 3-5 are sectional side views of another embodiment of an electrosurgical instrument shown in three different positions and is constructed in accordance with the invention;

FIGS. 6 and 7 are enlarged schematic sectional side views of the electrosurgical instrument of FIGS. 3-5 in operation and is constructed in accordance with the invention.

DETAILED DESCRIPTION

Figure 8:
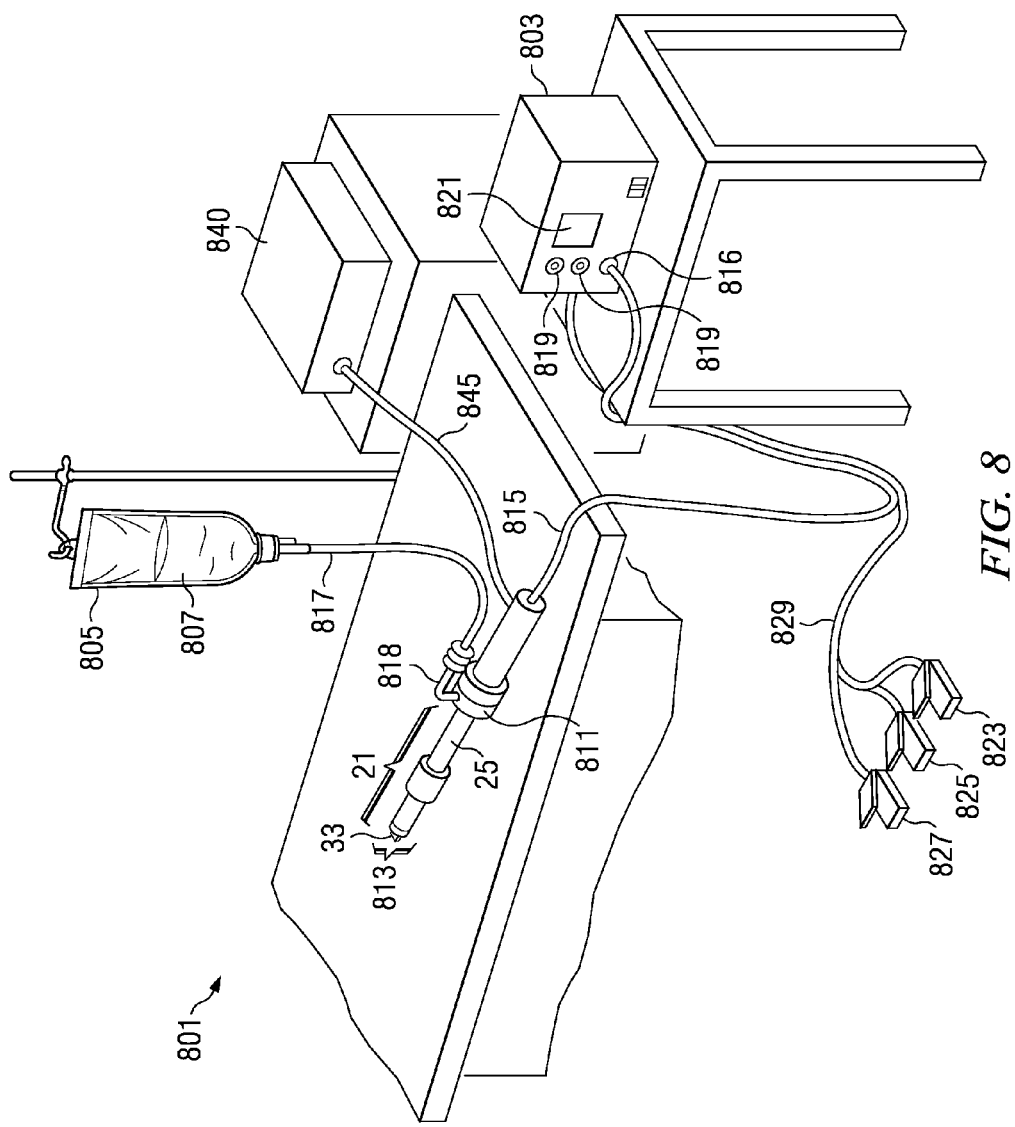
FIG. 8 is a schematic diagram of one embodiment of a system for operating an electrosurgical instrument and is constructed in accordance with the invention.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present disclosure may have a variety of configurations as described above. However, one variation employs a treatment device using Coblation® technology.

As stated above, the assignee of the present disclosure developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882 the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032, 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the present disclosure, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use according to the present disclosure may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one second interval that energy is applied) is on the order of about 50% for the present disclosure, as compared with pulsed lasers which typically have a duty cycle of about 0.0001%.

The preferred power source of the present disclosure delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Referring now to FIGS. 1-8, embodiments of a system, method and apparatus for an electrosurgical instrument having active and return electrodes with a movable suction sheath for variable fluid and debris removal during surgical procedures are disclosed. FIGS. 1 and 2 illustrate one embodiment of an electrosurgical suction apparatus 21 having an outer sheath 23 and grip 24 that is external to a shaft 25 to provide an annular fluid delivery channel 27 or lumen. The distal terminus of outer sheath 23 defines an annular fluid ingress 29 at a location proximal to return electrode 31.

The direction of flow of fluid and debris during use of apparatus 21 is indicated by the arrows. Electrically conductive fluid provided at the distal end of apparatus 21 forms a current flow path between active electrodes 33 and return electrode 31, and can facilitate generation of a plasma in the vicinity of active electrodes 33, as described hereinabove. Provision of an extraneous electrically conductive fluid may be particularly valuable in a dry field situation (e.g., in situations where there is a paucity of native electrically conductive bodily fluids, such as blood, synovial fluid, etc.). In an alternative embodiment, an electrically conductive fluid, such as saline, may be delivered to the distal end of suction apparatus 21 by a separate device (not shown).

The suction apparatus 21, or fluid and debris aspiration element, aspirates fluid and debris from a target site. For example, during an electrosurgical ablative procedure, it may be desirable to remove electrically conductive fluid, bodily fluids, resected tissue fragments and ablation by-products such as air bubbles from the target site to improve visibility and control the rate of ablation. The outer sheath 23, or sheath assembly, is disposed adjacent to the fluid aspiration element. The sheath assembly 23 is axially movable relative to the fluid aspiration element 21 between a first position (FIG. 1) for treating the target site and a second position (FIG. 2) for fluid and debris removal. The first position may comprise positioning a distal leading edge 29 of the sheath assembly 23 axially proximal to the distal end 33 of the shaft 25. The second position may comprise positioning the distal leading edge 29 of the sheath assembly 23 axially adjacent to the distal end 33 of the shaft 25, or alternatively axially distal to the distal end 33 of the shaft 25.

The fluid aspiration element 21 may comprise an inner lumen 35 extending through the shaft 25, and at least one port 37 (e.g., three shown) extending radially through the shaft 25. The port(s) 37 are in fluid communication with the inner lumen 35 as well as outer lumen 27, thereby creating an aspiration chamber under vacuum in the annular space surrounding shaft 25 and defined by sheath assembly 23 and seals 41. A vacuum source 39 (shown schematically) is connected to the inner lumen 35 for providing suction from outer lumen 27 through the port(s) 37 and inner lumen 35. The port 37 may comprise a plurality of ports that are located adjacent the distal end of the shaft 25 and axially spaced from the electrode assembly 31, 33.

In one embodiment, the sheath assembly 23 comprises a tube that is slidably movable relative to and concentric with the shaft 25. Grip 24 may be disposed on sheath assembly 23 in certain embodiments to provide an ergonomic interface for the user (e.g., with the user's finger) in order to ease movement and sliding of sheath assembly 23. The tube 23 defines an annular space or outer lumen 27 between the tube 23 and the shaft 25 and has a radial seal 41. The radial seal 41 is disposed between an outer surface of the shaft 25 and an inner surface of the tube 23 and sealingly engages the shaft 25 and the tube 23. The radial seal 41 may comprise a plurality of o-rings that are seated in an axial series of radial grooves 43 formed in the inner surface of the tube 23, with the radial grooves 43 being axially spaced from each other. The system may further comprising at least one spacer 45 (FIG. 2) located between the outer surface of the shaft 25 and the inner surface of the tube 23 for supporting and stabilizing the tube relative to the shaft along with the radial seal 41.

In the first position illustrated in FIG. 1, sheath assembly 23 is positioned to create a relatively low rate of suction from the target site and the area in the vicinity of the electrode terminal. In this first position, incidental fluid and debris are aspirated from the target site and adjacent to the electrode terminal. Additionally, the relatively low suction rate in the vicinity of active electrode 33 allows for the formation of an effective vapor layer and more efficient plasma for tissue treatment and ablation. Alternatively, in the second position illustrated in FIG. 2, edge 29 of sheath assembly 23 is positioned adjacent to or distal to active electrode 33 to create a larger aspiration field and a relatively higher suction rate from the target site and in vicinity of active electrode 33. In this second position, sheath assembly 23 is deployed for a considerable rate of aspiration and to focus on the aspiration of fluid and debris from the target site and adjacent to active electrode 33. Further, sheath assembly 23 may be deployed in the second position illustrated in FIG. 2 if the user detects the ablative effect on the target tissue is too intense, as the increased aspiration may mitigate the efficacy of the vapor layer and plasma formed at active electrode 33.

Referring now to the embodiments of FIGS. 3-7, the sheath assembly 123 may be provided with a range of motion between the first and second positions that provides a variable level of fluid and debris removal. Sheath assembly 123 is preferably slidable between a first deployed position where a minimal level of fluid and debris removal occurs (FIGS. 3 and 6), to a second deployed position where a maximum level of fluid and debris removal occurs (FIGS. 5 and 7). An intermediate level of fluid and debris removal is depicted in FIG. 4.

In these embodiments, the fluid aspiration element 121 comprises an inner lumen 135 extending through a portion of the shaft 125 and having an opening 134 at the distal end of shaft 125, and first and second ports 137, 138 extending radially through the shaft 125 in fluid communication with the inner lumen 135. The first and second ports 137, 138 are located on or adjacent to opposite axial ends of the inner lumen 135. The sheath assembly 123 comprises a tube that is slidably movable relative to and concentric with the shaft 125. Grip 124 may be disposed on sheath assembly 123 in certain embodiments to provide an ergonomic interface for the user (e.g., with the user's finger) in order to ease movement and sliding of sheath assembly 123. The tube 123 defines an annular space or outer lumen 127 between the tube 123 and the shaft 125 and has a radial seal 141. The radial seal 141 is disposed in the outer lumen 127 between an outer surface of the shaft 125 and an inner surface of the tube 123 and sealingly engages the shaft 125 and the tube 123.

A vacuum source 139 (e.g., indicated schematically) is connected to the inner lumen 135 and to the outer lumen 127 proximal to the radial seal 141. Referring now to FIG. 3, sheath assembly 123 is deployed such that seals 141 are disposed proximally of both the first and second ports 137, 138. In this configuration, no aspiration chamber is formed in the annular space between sheath assembly 123 and shaft 125 and distal seals 141, such that aspiration is provided only through opening 134 and inner lumen 135. In this configuration, first and second ports 137, 138 are at the same pressure with no net fluid flow therebetween and thereby fluidly bypassed by way of seals 141 isolating the first and second ports 137, 138 from the aspiration chamber and the portion of outer lumen 127 connected to vacuum source 139. When the sheath assembly 123 is in the intermediate position (FIG. 4) or in the second position (FIGS. 5 and 7), the vacuum source 139 provides a sequential suction path through inner lumen 135 via opening 134 as well as the outer lumen 127a that is distal to the radial seal 141, the first port 137, the inner lumen 135, the second port 138 and the outer lumen 127b proximal to the radial seal 141. Specifically, when sheath assembly 123 is disposed in the second position as depicted by FIG. 5, first port 137 and second port 137 are at different pressures creating an aspiration chamber under vacuum distal of seals 141 and allowing for net fluid flow between first port 137 and second port 138. As such, in this embodiment suction is available through both opening 134 and inner lumen 135 as well as through sheath assembly 123 and outer lumen 127. Further, the suction may be switched between inner lumen 135 via opening 134 or in combination with sheath assembly 123 and outer lumen 127. The first and second ports 137, 138 each may comprise a plurality of ports, with the first ports 137 being located adjacent the distal end of the shaft 125 and axially spaced from the electrode assembly 131, 133, and the second ports 138 being located proximal to the first ports 137.

In the first position illustrated in FIGS. 3 and 6, sheath assembly 123 is positioned to create a relatively low rate of suction through inner lumen 135 via opening 134 from the target site and the area in the vicinity of the electrode terminal. In this first position, incidental fluid and debris are aspirated from the target site and adjacent to the electrode terminal. Additionally, the relatively low suction rate in the vicinity of active electrode 133 allows for the formation of an effective vapor layer and more efficient plasma for tissue treatment and ablation. Alternatively, in the second position illustrated in FIGS. 5 and 7, a distal edge of sheath assembly 123 is positioned adjacent to or distal to active electrode 133 and in proximity to the target site to create a more aggressive aspiration field and a relatively higher suction rate from the target site and in vicinity of active electrode 133. In this second position, aspiration is available through both inner lumen 135 via opening 134 as well as outer lumen 127 via first and second ports 137, 138. As such, sheath assembly 123 is deployed for a considerable rate of aspiration and to focus on the aspiration of fluid and debris from the target site and adjacent to active electrode 133. Further, sheath assembly 123 may be deployed in the second position illustrated in FIGS. 5 and 7 if the user detects the ablative effect on the target tissue is too intense, as the increased aspiration may mitigate the efficacy of the vapor layer and plasma formed at active electrode 133.

Referring now to FIG. 8, an exemplary electrosurgical system 801 for treatment of tissue in "dry fields" is shown. System 801 also may be used in a "wet field," i.e., the target site is immersed in electrically conductive fluid. However, this system is particularly useful in dry fields where the fluid is preferably delivered through an electrosurgical probe to the target site. As shown, electrosurgical system 801 generally comprises an electrosurgical hand piece or probe 21 connected to a power supply 803 for providing high frequency voltage to a target site and a fluid source 805 for supplying electrically conductive fluid 807 to probe 21. In addition, electrosurgical system 801 may include an endoscope (not shown) with a fiber optic head light for viewing the surgical site, particularly in sinus procedures or procedures in the ear or the back of the mouth. The endoscope may be integral with probe 21, or it may be part of a separate instrument.

As shown, probe 21 generally includes a proximal handle 811 and an elongate shaft 25 having an array 813 of active electrodes 33 at its distal end. A connecting cable 815 has a connector 816 for electrically coupling the active electrodes 33 to power supply 803. The active electrodes 33 are electrically isolated from each other and each of the terminals is connected to an active or passive control network within power supply 803 by means of a plurality of individually insulated conductors (not shown). A fluid supply tube 817 is connected to a fluid tube 818 of probe 21 for supplying electrically conductive fluid 807 to the target site.

The system 801 also includes a vacuum source as described herein that is coupled to a suction lumen or tube in the probe 21 for aspirating the target site. Suction tube 845 is fluidly coupled with inner lumen 35 of probe 21 and in communication with suction pump 840 to thereby provide vacuum source 39 previously referenced herein. Suction pump 840 may encompass any suitable fluid transport apparatus. Suction pump 840 may comprise a positive displacement pump such as, for example, a peristaltic pump. In some embodiments the suction pump 840 may comprise a vacuum pump and canister assembly such as may be provided via a wall outlet in a surgical suite.

Power supply 803 may comprise an operator controllable voltage level adjustment 819 to change the applied voltage level, which is observable at a voltage level display 821. Power supply 803 also includes first, second and third foot pedals 823, 825, 827 and a cable 829 that is removably coupled to power supply 803. The foot pedals 823, 825, 827 allow the surgeon to remotely adjust the energy level applied to active electrodes 33. In an exemplary embodiment, first foot pedal 823 is used to place the power supply into the ablation mode and second foot pedal 825 places power supply 803 into the "coagulation" mode. The third foot pedal 827 allows the user to adjust the voltage level within the "ablation" mode.

In the ablation mode, a sufficient voltage is applied to the active electrodes to establish the requisite conditions for molecular dissociation of the tissue (i.e., vaporizing a portion of the electrically conductive fluid, ionizing charged particles within the vapor layer, and accelerating these charged particles against the tissue). As discussed above, the requisite voltage level for ablation will vary depending on the number, size, shape and spacing of the electrodes, the distance to which the electrodes extend from the support member, etc. Once the surgeon places the power supply in the ablation mode, voltage level adjustment 819 or third foot pedal 827 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 803 applies a low enough voltage to the active electrodes (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 823, 825, respectively. This allows the surgeon to quickly move between coagulation and ablation in situ, without having to remove his/her concentration from the surgical field or without having to request an assistant to switch the power supply.

By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply actuate foot pedal 825, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by actuating foot pedal 823.

Figure 9:
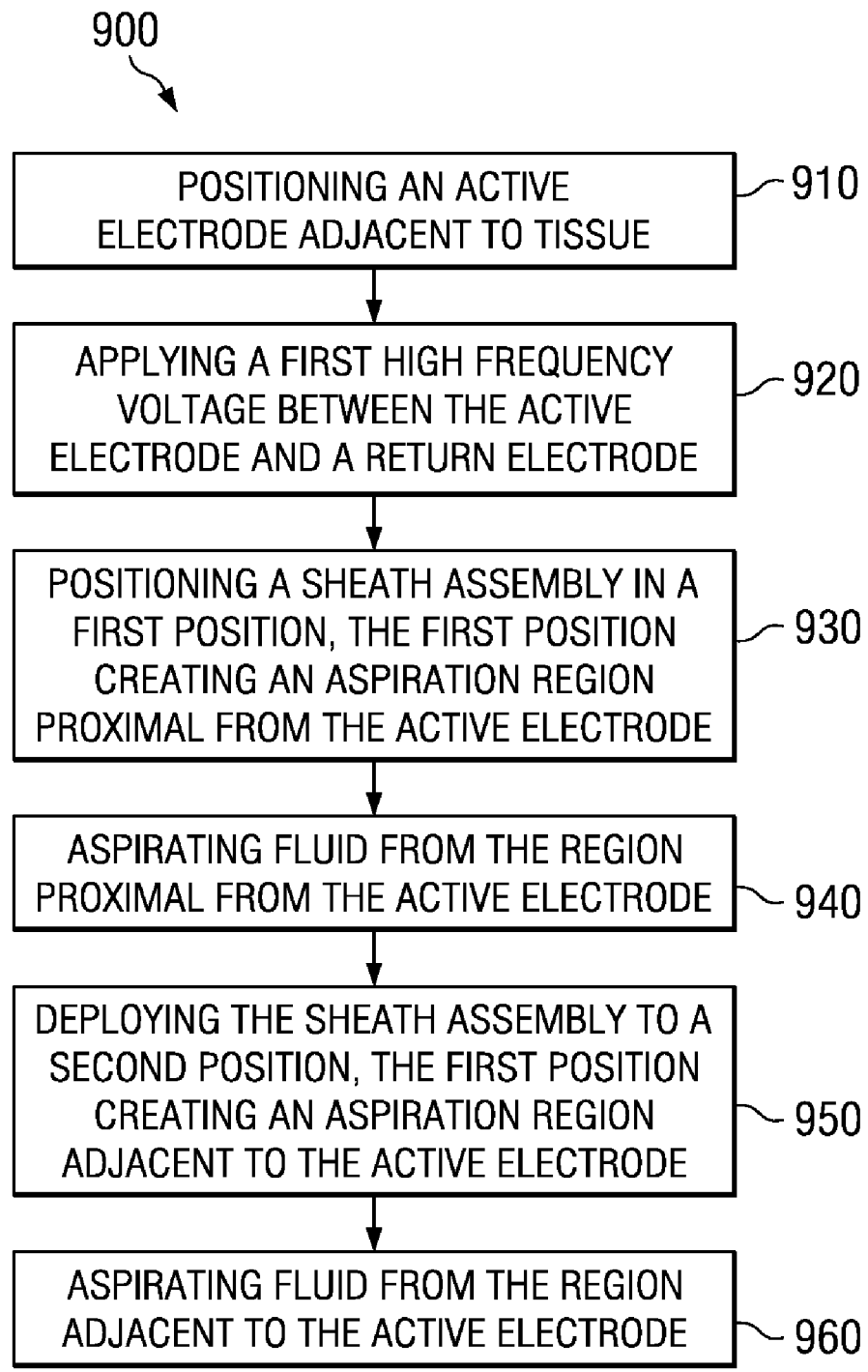
FIG. 9 shows a method in accordance with at least some embodiments.

Referring now to FIG. 9, a method (900) for treating tissue in accordance with at least some of the embodiments described herein is illustrated, including the steps of: positioning an active electrode adjacent to tissue (910); applying a first high frequency voltage between the active electrode and a return electrode (920); positioning a sheath assembly in a first position, the first position creating an aspiration region proximal from the active electrode (930); aspirating fluid from the region proximal from the active electrode (940); deploying the sheath assembly to a second position, the first position creating an aspiration region adjacent to the active electrode (950); aspirating fluid from the region adjacent to the active (960).

While the invention has been shown or described in only some of its forms, it should be apparent to those skilled in the art that it is not so limited, but is susceptible to various changes without departing from the scope of the invention.

We claim:

1. A system for treating tissue, comprising:
an electrosurgical instrument having a shaft with a proximal end and a distal end;
an electrode assembly comprising at least one active electrode positioned on the distal end of the shaft and a return electrode positioned on the shaft and axially spaced from the at least one active electrode;
an aspiration element for aspirating fluid and debris from a target site, the aspiration element comprising an inner lumen extending through a portion of the shaft, first and second ports extending radially through the shaft in fluid communication with the inner lumen, wherein the first and second ports are axially spaced apart; and a sheath assembly disposed adjacent to the aspiration element, the sheath assembly defining an annular space around the shaft and being axially movable relative to the aspiration element between a first position and a second position, wherein at least one radial seal is disposed within the annular space;

wherein the sheath assembly in the second position disposes the radial seal adjacent the second port and the sheath assembly in the first position spaces the radial seal proximally from the second port.

2. A system according to claim 1, wherein a distal leading edge of the sheath assembly is disposed axially proximal to the distal end of the shaft in the first position, and the distal leading edge of the sheath assembly is disposed substantially axially adjacent to the distal end of the shaft in the second position.

3. A system according to claim 1, further comprising a vacuum source connected to the inner lumen for providing suction through the first and second ports and inner lumen.

4. A system according to claim 1, wherein the first and second ports each comprise a plurality of ports that are located adjacent the distal end of the shaft and axially spaced from the electrode assembly.

5. A system according to claim 1 wherein the sheath assembly comprises an elongate tube that is slidably movable relative to and concentric with the shaft, the tube having a distal terminus moveable so as to be disposed adjacent the electrosurgical instrument distal end and wherein the tube defines an outer lumen for annular fluid flow between the elongate tube and the shaft, the radial seal being disposed between an outer surface of the shaft and an inner surface of the tube and sealingly engaging the shaft and the tube.

6. A system according to claim 5, wherein the radial seal comprises a plurality of o-rings that are seated in an axial series of radial grooves formed in the inner surface of the tube, the radial grooves being axially spaced from each other.

7. A system according to claim 1, wherein the first position is operable to aspirate at a distance spaced away from the active electrode and the second position is operable to aspirate adjacent to the active electrode.

8. A system according to claim 1, wherein the sheath assembly has a range of motion between the first and second positions that provides a variable level of fluid and debris removal, from a minimal level of fluid and debris removal in the first position, to a maximum level of fluid and debris removal in the second position.

9. A system for treating tissue, comprising:
an electrosurgical instrument having a shaft with a proximal end and a distal end;
an electrode assembly comprising at least one active electrode positioned on the distal end of the shaft and a return electrode positioned on the shaft and axially spaced from the at least one active electrode;
an aspiration element for aspirating fluid and debris from a target site comprising an inner lumen extending through a portion of the shaft, and first and second ports extending radially through the shaft in fluid communication with the inner lumen, the first and second ports axially spaced apart;
a sheath assembly disposed adjacent to the aspiration element, the sheath assembly defining an annular space around the shaft and being axially movable relative to the aspiration element between a first position and a second position;
wherein the sheath assembly comprises a tube that is slidably movable relative to and concentric with the shaft, the tube defining an outer lumen between the tube and the shaft and having at least one radial seal, the at least one radial seal being disposed in the outer lumen between an outer surface of the shaft and an inner surface of the tube and sealingly engaging the shaft and the tube;

and further comprising:
a vacuum source connected to the inner lumen; and
the vacuum source connected to the outer lumen proximal to the radial seal and, when the sheath assembly is in the second position, the vacuum source provides a sequential suction path through the inner lumen via a distal opening disposed at the distal end of the shaft, the outer lumen that is distal to the radial seal, the first port, the second port, and the outer lumen proximal to the radial seal.

10. A system according to claim 9, wherein the first and second ports each comprise a plurality of ports, with the first ports being located adjacent the distal end of the shaft and axially spaced from the electrode assembly, and the second ports being located proximal to the first ports.

11. An electrosurgical instrument for removing tissue from a target site within or on a patient's body comprising:
a shaft having proximal and distal end portions;
an electrode assembly comprising at least one active electrode positioned on the distal end portion of the shaft and a return electrode positioned on the shaft and axially spaced from the at least one active electrode;
an aspiration element for aspirating fluid and debris from the target site, the aspiration element coupled to a vacuum system, wherein the aspiration element comprises an inner lumen disposed in the shaft and a plurality of ports extending radially through the shaft and axially spaced from one another, the plurality of ports in fluid communication with the inner lumen; and
a movable sheath assembly disposed adjacent to the shaft and defining an annular space around the shaft, the sheath assembly comprising an elongate tube with a distal end portion movable from a first position wherein the distal end portion is retracted proximally from the electrode assembly to a second position wherein the distal end portion is adjacent to the electrode assembly;
wherein the elongate tube defines an outer lumen between the elongate tube and the shaft and wherein at least one radial seal is disposed between an outer surface of the shaft and an inner surface of the elongate tube to sealingly engage the shaft and the elongate tube.

12. The electrosurgical instrument of claim 11, the inner lumen having a distal opening.

13. An electrosurgical instrument for removing tissue from a target site within or on a patient's body comprising:
a shaft having proximal and distal end portions;
an electrode assembly comprising at least one active electrode positioned on the distal end port of the shaft and a return electrode positioned on the shaft and axially spaced from the at least one active electrode;
an aspiration element for aspirating fluid and debris from the target site, the aspiration element coupled to a vacuum system;
a movable sheath assembly disposed adjacent to the shaft and defining an annular space around the shaft, the sheath assembly having a distal end portion and being movable from a first position wherein the distal end portion is retracted proximally from the electrode assembly to a second position wherein the distal end portion is adjacent to the electrode assembly; and
wherein the sheath assembly comprises a tube that is slidably movable relative to and concentric with the shaft, the tube defining an outer lumen between the tube and the shaft and having at least one radial seal, the at least one radial seal being disposed between an outer surface of the shaft and an inner surface of the tube and sealingly engaging the shaft and the tube;

wherein the aspiration element comprises an inner lumen disposed in the shaft and a first and second plurality of ports extending radially through the shaft and axially spaced away from each other, the plurality of ports in fluid communication with the inner lumen and the annular space; and wherein the first and second plurality of ports are fluidly bypassed in the first position, and wherein the first and second plurality of ports are fluidly connected to the outer lumen proximal the at least one radial seal in the second position.

* * * * *

UNITED STATES PATENT AND TRADEMARK OFFICE
CERTIFICATE OF CORRECTION

| | | |
|---|---|---|
| PATENT NO. | : 8,317,786 B2 | |
| APPLICATION NO. | : 12/566913 | |
| DATED | : November 27, 2012 | |
| INVENTOR(S) | : Dahla et al. | |

It is certified that error appears in the above-identified patent and that said Letters Patent is hereby corrected as shown below:

Title Page

Item (73) Assignees name should be changed from "AthroCare Corporation, Austin, TX (US)" to --ArthroCare Corporation, Austin, TX (US)--.

In the Claims

Claim 5, Column 13, line 26, 28, 31 and 32, "the tube" should be changed to --the elongated tube--.

Signed and Sealed this
Fifteenth Day of October, 2013

Teresa Stanek Rea
*Deputy Director of the United States Patent and Trademark Office*